United States Patent [19]
Lowe et al.

[11] Patent Number: 6,046,246
[45] Date of Patent: Apr. 4, 2000

[54] PROCESS FOR MAKING FLUORINATED POLYMER ADSORBENT PARTICLES

[75] Inventors: Christopher Lowe, Cambs; Julie Tucker, Kent, both of United Kingdom

[73] Assignee: ProMetic Biosciences, Inc., Montreal, Canada

[21] Appl. No.: 09/329,289

[22] Filed: Jun. 10, 1999

Related U.S. Application Data

[60] Provisional application No. 60/088,940, Jun. 11, 1998.
[51] Int. Cl.⁷ ........................................................ C08J 9/22
[52] U.S. Cl. ............................ 521/57; 210/634; 210/635; 210/638; 435/803; 521/61; 521/63; 521/64; 521/145; 521/149

[58] Field of Search .................................. 521/61, 63, 64, 521/57, 145, 149; 210/634, 635, 638; 435/803

[56] References Cited

U.S. PATENT DOCUMENTS

| | | | |
|---|---|---|---|
| 4,171,412 | 10/1979 | Coupek et al. | 521/149 |
| 4,192,784 | 3/1980 | Brown et al. | 521/149 |

*Primary Examiner*—Morton Foelak

[57] ABSTRACT

Chemically resistant, strong fluorinated copolymer adsorbent particles for use in carrying out chromatographic separations are prepared by high shear, anaerobic reaction of a di-unsaturated crosslinking agent with a polyfluorinated monomer in the presence of poly(vinyl alcohol) and a porogen.

16 Claims, No Drawings

PROCESS FOR MAKING FLUORINATED POLYMER ADSORBENT PARTICLES

This application claims priority benefit of U.S. Provisional Application No. 60/088,940, filed Jun. 11, 1998, now pending.

FIELD OF INVENTION

The invention relates to a process for making fluorinated polymer adsorbent particles and to their use as a stationary phase for carrying out chromatographic separations.

BACKGROUND OF THE INVENTION

Support materials for use in high productivity liquid chromatography must be mechanically strong in order to withstand operation at high rates of flow under high pressures. Moreover, such physical properties must be stable over the wide range of pH to which such materials are subjected during normal operation and regeneration. Physical properties of particular importance to chromatographic media are (1) sphericity of the particles, (2) high surface area, (3) high pore volume and availability with (4) a wide range of pore diameters, and (5) a wide range of particle diameters.

In seeking these goals, a wide variety of polyfluorocarbon substrates have been developed by others, but these developments have achieved only limited success in their capability of meeting each of these criteria. The particles of the invention constitute a major improvement over the prior art, especially with respect to higher surface areas, higher pore volume and high porosity.

SUMMARY OF THE INVENTION

The invention is therefore directed to the manufacture of fluorinated adsorbent particles which meet all the above-described criteria for superior performance as the stationary phase for use in chromatographic separations.

In a first aspect, the invention is directed to a process for the preparation of porous spherical particles of fluorinated polymer adsorbent comprising the steps:

(1) forming a water-insoluble solution of organic compounds comprising (a) a monomer selected from $C_{2-4}$ alkylene glycol ester of a $C_{3-6}$ acrylic acid, (b) a polyfluorinated vinyl monomer, (c) a free radical initiator and (d) a water-insoluble, organic solvent-soluble porogenic material, the weight ratio of comonomers (a) and (b) to the porogenic material being 0.5–2;

(2) with high shear agitation, forming a dilute solution of poly(vinyl alcohol) in water from which any oxygen has been purged with inert gas;

(3) with continuing high shear agitation and inert gas purging, rapidly dispersing the water-insoluble solution of organic compounds from step (1) into the dilute aqueous poly(vinyl alcohol) solution from step (2) and, as necessary, adjusting the temperature of the dispersion to 30–90 C. to initiate copolymerization of the monomers, the level of high shear mixing energy being sufficient to disperse the water-insoluble solution of organic compounds in the poly(vinyl alcohol) solution in the form of liquid droplets having an average diameter of no more than 10–50 micrometers, at least 90% of the droplets being within 40% above or below the average mean particle diameter;

(4) continuing the high shear agitation and oxygen purging of the dispersion from step (3) for a time sufficient to effect complete copolymerization of the monomers and particulation of the droplets in the form of finely divided polymer particles by precipitation of the copolymer therein;

(5) separating the finely divided copolymer particles from the polymerization reaction medium;

(6) extracting the porogenic material from the separated copolymer particles of step (5) by washing the particles with inert organic solvent, thereby forming pores within the copolymer; and (7) drying the porous copolymer particles.

In a second aspect, the invention is directed to adsorbent particles made by the above-described process.

In a further aspect, the invention is directed to the use of the abovedescribed adsorbent particles as the stationary phase for carrying out chromatographic separations.

DETAILED DESCRIPTION OF THE INVENTION

Introduction: As summarized above, the invention is directed primarily to a method for making high quality adsorbent fluoropolymer particles by suspension polymerization with an aqueous poly(vinyl alcohol) medium. The basic components of the process are (1) the water-insoluble polymerization system, which is comprised mainly of a polyfluorinated monomer, a non-fluorinated comonomer and a free radical-initiating catalyst, and (2) the dispersion medium, which is a dilute aqueous solution of poly(vinyl alcohol) [PVA].

A. Poly(vinyl alcohol)

While it is conventional to conduct suspension polymerizations in an aqueous medium, it is essential that the polymerization of the polyfluorinated copolymer for use in the invention be conducted in the presence of a dilute aqueous solution of poly(vinyl alcohol), hereinafter referred to as PVA. The principal function of the PVA is to adjust the interfacial surface tension between the finely dispersed water-insoluble polymerization components and the continuous aqueous medium phase. By regulating the concentration of PVA dissolved in the aqueous medium, the droplet size of the dispersed polymerization system and thus the size of the resultant polymerized particles can be more finely controlled.

So long as the PVA is essentially completely dissolved in the aqueous medium, a wide range of PVA molecular weights can be used successfully in the practice of the invention. It is, however, preferred that the PVA be at least 80% hydrolyzed, and more preferably at least 86% hydrolyzed, with a molecular weight of at least about 1,000. As stated above, the maximum usable molecular weight is a function of the ambient water solubility of the PVA. The molecular weight of the PVA will ordinarily not exceed 150,000 and preferably is no higher than 100,000.

For the purposes of the invention, the concentration of PVA in the aqueous medium should be within the range of 1 to 50 mL PVA per liter of water. Below 1 mL/L the modifying effect of the PVA is insufficient and above about 50 mL/L no further advantage is discernible. It is, of course, desirable to use lesser amounts of PVA in order to avoid energy-wasting increases in viscosity of the aqueous medium.

B. Polymerization System

1. Polyfluorinated monomer

As set out above, the fluorine-containing comonomer must contain a plurality of fluorine (F) substituents. However, the comonomer need not be perfluorinated.

Nevertheless, it is preferred that the fluorinated comonomer contain at least three F substitutions. In addition to these restrictions on its degree of fluorination, it is essential that the fluorinated comonomer be essentially completely insoluble in water under the polymerization temperatures encountered and essentially completely soluble in the other components of the dispersed polymerization system.

Suitable polyfluorinated comonomers are those containing active vinyl sites such as acrylates, methacrylates, vinyl compounds, maleates and itaconates. Among the many compounds within those categories are pentafluorostyrene, bis-hexafluoroisopropyl itaconate, bis-hexafluoroisopropyl maleate, heptadecafluorodecyl acrylate, perfluorooctyl methacrylate, 2,2,3,3-tetrafluoropropyl methacrylate, monotrifluoroethyl itaconate, 2,2,2-trifluoroethyl maleate, vinyl benzyl perfluoroctanoate and vinyl trifluoroacetate.

2. Non-fluorinated comonomer

It is preferred that the comonomer component of the polyfluorinated copolymer for use in the invention be a non-fluorinated $C_{2-4}$ alkylene glycol ester of a $C_{3-6}$ acrylic acid. The comonomer must have at least two vinyl groups. Suitable comonomers having this composition are ethyleneglycol dimethacrylate, 1,3-propyleneglycol dimethacrylate, 1,4-butanediol dimethacrylate, ethyleneglycol itaconate, ethyleneglycol diacrylate, and ethyleneglycol dimaleate. Divinyl benzene can also be used for this purpose.

3. Free Radical Initiator

An essential component of the polymerization is a source of free radicals. In particular, the system must contain one or more compounds which thermally decompose under the conditions of polymerization to form free radical species. A preferred free radial agent is a mixture of azo-bis-isobutyronitrile and benzoyl peroxide. From about 10 to about 50 mg/L are needed for this purpose. It is recognized that higher concentrations are operable functionally. However, it is preferred to use as small amounts as possible in order to lessen the amount of extraneous materials in the formed polymer particles.

C. Porogen

Suitable porogenic materials are those organic compounds which are (1) chemically inert with respect to the other components of the polymerization phase, (2) completely soluble in the polymerization system, (3) completely insoluble in the continuous aqueous phase and (4) readily extractable from the polymerized particles at relatively low temperatures with a low molecular weight organic solvent. Dibutyl phthallate, which is easily removed by washing the polymer particles with dichloromethane, is a preferred porogen for use in the invention. Other suitable porogens include toluene, isopropyl benzene 2-methyl-4-pentanone, 2-methyl-4-pentanol and chlorobenzene.

D. Polymerization Procedure

The operating conditions for use in the process of the invention are quite specifically defined because they are essential to obtaining adsorbent particles having suitable properties.

Firstly, it is essential that the polymerization procedure be conducted in the essentially complete absence of air or any other source of oxygen contamination, which might lead to adverse reactions with any of the components of the polymerization system, especially the monomers, crosslinking agent and free radical initiator. It has been found that the most practical way of removing and preventing the introduction of oxygen into the polymerization system is continuously to purge the polymerization reaction system before, during, and after completion of the polymerization process with an inert gas. Any of the inert gases are, of course, suitable for this purpose. However, argon and nitrogen are the least expensive and will therefore be preferred in most instances. Because the polymerization is conducted under very high energy mixing conditions, the method of introducing the purging gas is not particularly critical, so long as it is adequate in volume.

As mentioned above, the PVA functions principally for more precise control of interfacial tension between the dispersed monomer droplets and the aqueous PVA continuous medium. The droplet size is controlled more dominantly by the amount of mixing energy used to disperse the polymerization system. Thus, only comparatively low concentrations of PVA are required in the aqueous medium, e.g., on the order of 1–100 g/L. A PVA concentration within the range of 0.5–40 g/L is preferred. Though higher concentrations can be used, they do not improve functionality. Because of the necessity of forming very small droplets during the polymerization, it is, of course, desirable to avoid higher PVA concentrations which would render the aqueous medium more viscous.

The amount of energy input into the polymerization is primarily a function of the polymer particle size which is desired. Thus, if larger particles are sought, the degree of mixing (energy input) is lowered. If smaller particles are sought, the degree of mixing is raised. As discussed hereinabove, it is preferred that droplet size during polymerization be controlled to obtain polymer particles within the range of 5–300 micrometers, 20–100 micrometers being especially preferred.

F. Particle Properties

As set out hereinabove in the Background of the Invention, ideal chromatography media need to have the following properties: (1) spherical shape; (2) high surface area; availability of a wide range of (3) pore diameters and (4) particle diameters; (5) high pore volume; (6) high mechanical strength; and (7) both chemical and mechanical stability throughout the pH range to which the media are exposed in use.

Sphericity of the particles, rather than irregular, granular shapes, is needed to provide minimum resistance to flow through a packed bed of the particles and minimum back pressure. Such regularly shaped particles are less likely to undergo densification during use.

Particle size and size distribution are also important properties of the particles of the invention. In general, particles larger than about 20 micrometers facilitate lower back pressure in packed columns. Moreover, the chromatographic peak width and peak shape obtained with larger particles are usually wider than the peak width and shape obtained with particles in the range of 3–15 micrometers. Narrow peak shapes are frequently desired for many types of separations.

The available surface area of polyfluorinated particles produced by the method of the invention is ordinarily preferred to be at least about 200 $m^2/g$ in order to obtain higher loading of antigens on the particulate media. Nevertheless, media having much lower surface areas can readily be made according to the invention by changing the amount of porogen used in the polymerization system and decreasing the size of the particles. Concomitantly, a large pore volume of at least 0.5 mL/g is needed in order to obtain a high surface area.

A wide range of pore sizes must be available for different chromatographic procedures. Large pores are, of course, needed for the efficient capture of larger molecules, such as proteins, while small pores are needed for the efficient capture of small molecules. In general, the range of pore sizes may extend from below 60 Å to as high as 1,000 Å, 300–800 Å being preferred. This range of sizes is quite readily available using the invention method of adjusting the relative amount and type of porogen within the formed polymer particles.

Because of the wide range of pH values at which chromatography media are used and because of the very high pH ranges which are encountered frequently to clean and regenerate them, it is necessary that they be chemically inert throughout the entire range of such pH exposures. In particular, chromatographic media must be able to withstand the high pH (12 or higher) encountered by the use of NaOH for cleaning the media particles, typically 0.1–1 normal.

The polyfluorinated particles of the invention can be used for chromatographic separations either with or without a coating of a hydrophilic polymer, such as poly(vinyl alcohol). The adsorbent particles of the invention are quite versatile and can be used to carry out a wide variety of chromatographic separations, including reverse phase separations, affinity separations and expanded bed separations.

The surface chemistry of the uncoated particles is hydrophobic, but with a slight polarity, which combination of properties is ideal for reverse phase chromatographic separations. Reverse phase chromatography involves the use of a relatively non-polar stationary phase in conjunction with a very polar mobile phase that is usually water. This technique is used to separate solutes of lower polarity. Reverse phase chromatography is usually performed using silica that is coated with an organic silane to provide hydrophobicity. However, the hyrophobized silica has a severe limitation in that it cannot be used at pH greater than 11 and cannot be cleaned with concentrated caustic soda solutions without dissolving the particles. A substantial advantage of the polyfluorinated particles of the invention is that they do not have this limitation.

The use of the uncoated invention particles for reverse phase chromatography is illustrated by Example 26 and the exceptional stability of the particles of the invention toward basic solutions is shown by the data obtained in Example 27 below.

Suitable hydrophilic polymers for use in coating the polyfluorinated particles of the invention are those which are uncharged, water-soluble, non-cyclic and have a multiplicity of hydroxyl groups. Though many several such hydrophilic polymers are useful for this particular function, poly(vinyl alcohol) is preferred.

G. Derivatization of Particles

If desired, the PVA-coated polyfluorinated particles can be functionalized by reacting suitable molecules with the hydroxyl groups of the PVA. Thus, strong cationic ion exchange functionality can be provided to the particle surfaces by placing sulfonic acid groups on the surface. Likewise, strong anionic ion exchange functionality can be provided by applying quaternary amines. Weak cation functionality can be produced by the use of carboxylic groups and weak anion functionality can be obtained by the use of primary amines.

EXAMPLES

Example 1

A porous copolymer of ethyleneglycol dimethacrylate and pentafluorostyrene was prepared in the following manner:

Four hundred ninety mL of distilled water were placed in a vessel and agitated with a high efficiency paddle mixer at 800 rpm. With continuing agitation, argon gas was added to purge oxygen from the water and 3.9 g of poly(vinyl alcohol) were added to the water. Agitation and purging were continued for 30 minutes, during which vortexing of the mixture was reduced by changing the angle of the agitator. Ethyleneglycol dimethacrylate (55.7 g) and pentafluorostyrene (39.8 g) were mixed together and 127 mL of dibutylphthalate were added to the mixture after which 0.48 g azo-bis-isobutyronitrile and 0.45 g of benzoyl peroxide were added. The mixture was then stirred until homogeneous. The thusly prepared homogeneous mixture was then added rapidly to the aqueous poly(vinyl alcohol) solution and the resultant polymerization mixture was heated to about 80 C. Agitation at 800 rpm and argon purging were continued throughout until the polymerization was complete.

Upon separating the thusly formed fluoropolymer particles from the polymerization medium, they were washed sequentially with (1) 200 mL of distilled water at 60 C. (2) 200 mL of acetone at 60 C. and (3) 200 mL of a 30/70% by volume mixture of hot water and acetone at 70 C. Upon completion of the washing steps, the particles were dried overnight in an oven at 70 C.

The washed and dried fluoropolymer particles were then refluxed with 10% wt. dichloromethane for 6–7 hours at 50 C. to remove the porogenic material from the particles. The porogen-free particles were placed on a sintered glass funnel and rinsed with 50 mL acetone per gram of particles, after which the rinsed particles were dried overnight at 70 C.

The washed polyfluorinated particles had an average particle size of 51 micrometers, surface area of 300 $m^2/g$ and pore volume of 1.0 mL/g. Thus, the procedure was quite effective in making spherical porous particles of pentafluorostyrene.

Example 2

A porous copolymer of ethyleneglycol dimethacrylate and 2-(N-ethyl perfluoro octane sulfo amido) perfluoromethacrylate was prepared in the following manner:

Set-up

1 L. cylindrical reactor fitted with a "type E" agitator (Cole Palmer, 6 cm diameter and 10 cm height), reflux condenser, gas inlet tube and immersed temperature probe. The agitator is positioned so that its top impeller blade is located just above the level of the aqueous phase.

Aqueous phase 3.9 g PVA (Adrich, 85,000 to 146,000 Daltons, 97–99% hydrolyzed) in 490 mL DI water Organic phase 1.7 g of polystyrene (Aldrich, 90,000 MW standard)
171 mL isopropyl benzene (Aldrich, 99%)
85.6 g ethylene glycol dimethacrylate (Aldrich, 98%, 100 ppm MEHQ)
85.6 g 2-(n-ethylperfluorooctane sulphonamido) ethyl methacrylate (Monomers, Polymers and Dajack)
0.57 g AIBN (Aldrich, 99%)
1.14 g BPO (Aldrich, 98%)

Procedure

The aqueous phase was prepared by predissolving the PVA in water at approximately 50 C. The aqueous phase was charged to the reactor and sparged with nitrogen for 25 minutes.

The polystyrene was pre-dissolved in the isopropyl benzene. The mixture of the two monomers was then added, followed by the initiators. After stirring for 1 hour, the organic phase still appeared cloudy and was added as such to the reactor. Under a nitrogen sweep, the mixture was stirred at 800 rpm and heated to 80 C. over a period of 30 minutes. Upon reaching reaction temperature, most of the organic phase agglomerated into a single mass which broke up into individual beads again after 25 minutes.

After 9 hours at reaction temperature, the system was allowed to cool, the aqueous phase siphoned out and the resin beads washed with 500 mL DI water, 500 mL acetone, 500 mL acetone water (30:70), 500 mL hot water and twice with 500 mL acetone.

After air drying, the resin weight is 168 g.

The resin is refluxed for 5 hours in 1 L methylene chloride, washed with 1 L acetone and air dried.

The washed and dried fluoropolymer particles were then refluxed with 10% wt. dichloromethane for 6–7 hours at 50 C. to remove the porogenic material from the particles. The porogen-free particles were placed on a sintered glass funnel and rinsed with 50 mL acetone per gram of particles, after which the rinsed particles were dried overnight at 70 C.

The procedure was very effective for making porous spherical particles of perfluoromethacrylate.

Example 3

Coating of Styrenic Fluoropolymer Particles with PVA

Using dry fluoropolymer particles prepared in the manner of Example 1, 50 g of such particles were de-agglomerated by sonication in methanol for 5 minutes and soaked overnight in 150 mL of methanol. This de-agglomeration step was carried out in separate batches of 2 g resin in 20 mL methanol.

The methanol resin slurry was placed in a 3 L round bottom flask and enough methanol siphoned out so that it just covered the beads. A solution of 80 g PVA (31,000 to 50,000 Daltons, 98% hydrolyzed) in 1 L deionized water, previously prepared by dissolving the PVA at 50 C. was then added to the flask and the resulting slurry stirred at room temperature for 24 hours. After collecting a sample for PVA content analysis, the loading solution was separated from the beads by decantation. The beads were transferred to a fritted funnel and washed twice for 10 minutes with 500 mL deionized water, followed by removal of the water by suction. The water washes were combined and a sample retained for PVA content analysis. The washed beads were returned to the round bottom flask, and 1 L of deionized water was added. Stirring was resumed, and 1 mL of 50% aqueous solution of glutaraldehyde was added, immediately followed by 8 mL of 5 N aqueous HCl. After stirring for an additional 24 hours at room temperature, the beads were transferred to a fritted funnel, drained, washed three times with 1 L deionized water and set aside as a wet slurry.

This example shows that spherical polyfluorinated particles made in accordance with the invention can be readily coated with poly(vinyl alcohol) in this manner.

Example 4

Coating of Styrenic Fluoropolymer Particles with PVA

Again using dry fluoropolymer particles prepared in the manner of Example 1, 50 g of the particles were soaked in methanol and coated with PVA in the manner of Example 3, except that the concentration of the PVA in the aqueous solution was raised to 20 g/L.

Example 5

Coating of Methacrylic Fluoropolymer Particles with PVA

In this Example, 50 g of fluoropolymer particles prepared in the manner of Example 2 were coated with PVA in the manner of Example 3.

Example 6

Measurement of PVA Coating on Fluoropolymer Particles

The concentration of PVA was determined by measuring the absorbance of the PVA/iodine/boric acid complex measured at 690 nm and comparing it with a calibration curve prepared using standard PVA solutions. The linear range of the colorimetric assay is up to 1 mg PVA/mL. The amount of PVA adsorbed on the resin was determined by the difference of the initial coating solution concentration minus the final solution concentration. Results are reported in mg or g PVA/g dry resin.

For a 9.31 mg/mL PVA coating solution, dilute samples 100× with distilled water. Pipet 2.0 mL of the sample prepared in 1) into the cuvette along with 0.5 mL of the 0.6M boric acid solution and 0.1 mL of the KI/I$_2$ solution. Mix and let stand in the darkness for 30±5 min. before taking the absorbance rating at 690 nm. Calculate the weight of PVA adsorbed onto the fluoropolymer beads by the following relationship:

$$\text{mg PVA}/\text{g resin} = \frac{(Ci)(Vi) - (Cf)(Vf)}{W}$$

where,

Ci=Concentration (mg/mL) of initial PVA coating solution

Vi=Volume (mL) of PVA coating solution

Cf=Concentration (mg/mL) of PVA coating solution at the end of coating process

Vf=Final volume (mL) of coating solution

Vf may be greater than Vi due to a contribution from the wetting solvent

W=Weight (g) of dry fluoropolymer used in the coating process

Using this method, the amount of PVA adsorbed onto the perfluorinated polymers was measured at 0.4 g PVA per g of the dry fluoropolymer prepared as in Example 3 and 1.51 g PVA per g of the dry fluoropolymer prepared as in Example 5.

This example shows that the polyfluorinated polymer of the invention was well coated with poly(vinyl alcohol).

Example 7

Measurement of HSA Capacity of PVA-coated Fluoropolymer Particles

Fluoropolymer prepared and coated with a high level of PVA in the manner of Example 3 was tested with respect to their human serum albumin (HSA) capacity. In particular, 4 mL of a 4 mg/mL solution of HSA in 20 mM phosphate buffer at pH 7.4 were added to 0.5 g of PVA coated beads prepared as in Example 3 and the resulting slurry rotated on a flat bed mixer for 16 hours at room temperature. The concentration of HSA in the supernatant was then determined using the Bradford assay. The amount of protein non-specifically bound to the resin, calculated by difference, was 2 mg/g dry fluoropolymer.

This example shows clearly that protein will bind to the uncoated invention substrate more efficiently than to the corresponding coated substrate.

Example 8

Measurement of HAS Capacity of PVA-coated Fluoropolymer Particles

Fluoropolymer particles prepared and coated with a low level of PVA in the manner of Example 4 were tested with respect to their HAS capacity by the same procedure as Example 7. The amount of HAS adsorbed was determined to be 12.5 mg/g of dry resin.

The example shows that when poly(vinyl alcohol) is coated onto the polyfluorinated particles of the invention, it is a uniform, effective coating.

Example 9

Measurement of Lysozyme Capacity of PVA-Coated Fluoropolymer Particles

Fluoropolymer particles prepared and coated with a high level of PVA in the manner of Example 3 were tested with respect to their lysozyme capacity by the same procedure as Example 7. In particular, 4 mL of a 4 mg/mL-solution of lysozyme in 20 mM carbonate buffer at pH 9.0 was added to 0.5 g of PVA coated beads prepared as in Example 3. The resulting slurry was rotated on a flat bed mixer for 16 hours at room temperature. The concentration of lysozyme in the supernatant was then determined based on the supernatant's adsorption at 280 nm. The amount of protein non-specifically bound to the fluoropolymer beads, calculated by difference, was 5 mg/g dry resin.

Example 10

Size Exclusion Chromatography of Proteins

A 10 mL Pharmacia HR 10/30 column was packed with fluoropolymer particles prepared as in Example 3 and equilibrated with 20 nM phosphate buffer at pH 7.0. The column void volume (Vo) was determined by measuring the elution volume (Ve) of Blue Dextran 2000 (0.5 mL injection, 4 mg/mL, 20 mM phosphate buffer at pH 7.0). 0.05 mL of a 10 mg/mL each of ribonuclease A, ovalbumin and aldolase was loaded onto the column and eluted with the equilibration buffer at 0.02 mL/min. Similarly, a solution of chymotrypsinogen A and bovine serum albumin were loaded onto the column and eluted with the equilibration buffer at a flow rate of 0.02 mL/min. The elution volumes of the various proteins were measured from the chromatogram (UV detection) and their respective partition coefficients (Kav) calculated using the following equation:

$$Kav=(Ve-Vo)/(Vt-Vo)$$

where Vt is the total volume of the column.

The results, summarized in Table 1 below, show the expected inverse relationship between partition coefficient and molecular weight for globular proteins.

TABLE 1

| PROTEIN | MOLECULAR WEIGHT (Daltons) | PARTITION COEFFICIENT |
| --- | --- | --- |
| Ribonuclease A | 13,700 | 1 |
| Chymotrypsinogen A | 25,000 | 0.36 |
| Ovalbumin | 43,000 | 0.18 |
| Albumin | 67,000 | 0.13 |
| Aldolase | 158,000 | 0.07 |

Example 11

Binding of Blue Dye to PVA-coated Fluoropolymer Particles

This example was directed to the binding of a blue dye at low concentration on PVA-coated fluoropolymer particles.

To 1 mL of PVA-coated fluoropolymer beads prepared as in Example 3 were added a solution of 50 micromol (40 mg) of Cibacron Blue F3G-A in 8.4 mL of water and 250 microliters of 2M NaCl. After mixing for 30 minutes on a flat bed mixer, 500 micromoles of $Na_2CO_3$ were added and the slurry tumble-mixed for 16 hours at 80 C. The beads were then washed, retaining the filtrates, on a glass sinter with 50 mL each of water, 1 M NaCl, dimethylformamide, water, 3% (v/v) methanol/water, water, methanol, water, 1 M NaOh and finally 100 mL fractions of water until the filtrate became clear. The amount of Cibacron Blue F3G-A bound to the resin—15 micromol/mL was determined by measuring the dye concentration in the washing solutions, determined by adsorbance at 620 nm, and calculating the amount bound by difference.

Example 12

Binding of Blue Dye to PVA-coated Fluoropolymer Particles

This example was directed to binding Cibacron Blue F3G-A dye to a PVA-coated styrenic fluoropolymer particles with a high concentration of the blue dye. The resin was coated with the PVA in the manner of Example 6, except that the amount of water to dissolve the 50 Mmoles of blue dye was 1 mL. The dye was applied in the manner of Example 11. The resulting ligand density was 25 micromoles per mL of the fluoropolymer particles.

Example 13

Lysozyme Capacity of the Affinity Polymer

This example was carried out using a fluoropolymer prepared in the manner of Example 11, which contained a blue dye binding with low ligand density. A 1 mL Pharmacia HR 5/10 column was packed with a resin prepared as in Example 11 and equilibrated with sodium phosphate buffer (20 mM, pH 7.4). 4 mL of a 5 mg/mL solution of lysozyme in the equilibration buffer was loaded onto the resin at 1 mL/min. The lysozyme was then eluted from the resin using 1M NaCl in 20 mM sodium phosphate buffer, pH 7.4. The amount of lysozyme eluted, as determined by measuring the eluent's absorption at 280 nm, was 18 mg per mL of fluoropolymer.

This example should be compared with Example 9 where no blue dye was bonded to the poly(vinyl alcohol).

Example 14

Lysozyme Capacity of the Affinity Polymer

This example was carried out using a fluoropolymer prepared in the same manner as Example 12, but having a high ligand density. The amount of lysozyme eluted was 20 mg/mL of resin.

Example 15

Non-adsorption of Myoglobin by the Affinity Polymer

A fluoropolymer was prepared using the procedure of Example 12 using myoglobin as the protein. No protein adsorption by the polymer could be detected.

Example 16

Bed Expansion

In this test, a 40 cm×1 cm column was packed with fluoropolymer particles prepared in the manner of Example 12 and subsequently screened to a 63 to 82 micrometers particle diameter range. Water was pumped up-flow in the column and the bed expansion ration (the ratio of the bed depth at a given flow rate vs. bed depth without flow) He/Ho, measured at various flow rates. The results are summarized in Table 2.

TABLE 2

| Flow Rate (cm/h) | 8 | 25 | 40 | 55 | 68 |
|---|---|---|---|---|---|
| Bed Expansion ration (He/Ho) | 1.2 | 1.7 | 1.75 | 1.9 | 2.1 |

These data illustrate the advantageous use of the invention particles, which results from their higher density, i.e., 1.2 g/mL versus only 1.09 g/mL for prior art polymeric particles.

Examples 17–26

Chemical Stability of the Resin

A series of tests was carried out to determine the chemical stability of the adsorbent resin prepared in the manner of Example 1. For this series, 200 mg of fluoropolymer particles prepared as in Example 12 were soaked in 2 mL of the solvent indicated. Leakage of the Cibacron Blue F3G-A was checked over time by monitoring the supernatant adsorbance at 620 nm. The dye concentrations measured in the supernatant after 37 days are summarized in Table 3.

TABLE 3

|  | SOLVENT (micromol) | DYE CONCENTRATION |
|---|---|---|
| EXAMPLE 17 | 25% aq. glycerol | 0.008 |
| EXAMPLE 18 | 1% aq. sodium dodec. sulfate | 0.008 |
| EXAMPLE 19 | 8M urea | 0.004 |
| EXAMPLE 20 | 1M NaSCN | 0.01 |
| EXAMPLE 21 | 5M HCl | 0.002 |
| EXAMPLE 22 | dimethyl formamide | 0.01 |
| EXAMPLE 23 | methanol | n.d. |
| EXAMPLE 24 | acetone | n.d. |
| EXAMPLE 25 | water | 0.002 |

Example 26

The following test was carried out to show the use of the uncoated polyfluorinated particles of the invention for reverse-phase chromatography:

Polymer particles prepared in the manner of Examples 1 and 2 were packed at 1,600 psi into stainless steel columns of 250 cm length and 0.46 cm inside diameter. The slurry solvent was 50/50 by volume methanol/isopropanol. The gradient test mixture solvent was 50/50 by volume acetonitrile/water with 0.1 TFA. The mobile phase was A=water with 0.1% TFA, B-acetonitrile with 0.1% TFA. The test mixture was Vitamin B-12 (1.0 mg), bovine insulin (3.0 mg), ribonuclease A (3.0 mg), human albumin (3.0 mg) and thyroglobulin (3.0 mg). The retention times (minutes) comparing the effectiveness of methacrylic particles with the pentafluorostyrene polymer particles of the invention are set out in Table 4.

TABLE 4

EFFECTIVENESS OF PENTAFLUOROSTYRENE POLYMER AND FLUORINATED METHACRYLIC POLYMER SUBSTRATES IN REVERSE-PHASE CHROMATOGRAPHY

| Solute | Pentafluorostyrene Polymer (Retention time, minutes) | Fluorinated Methacrylic Polymer |
|---|---|---|
| Vitamin B-12 | 1.00 | 1.00 |
| Bovine insulin | 1.59 | 1.75 |
| Ribonucleose A | 1.83 | 2.02 |
| Human albumin | 2.08 | 2.32 |
| Thyloglobulin | 2.40 | 2.72 |

Correlation of the data showed that smooth, symmetrical, non-overlapping curves were obtained. The data therefore clearly demonstrate that both the uncoated pentafluorostyrene polymer and the uncoated fluorinated methacrylic polymer particles are effective media for the chromatographic separation of mixtures of materials such as proteins.

Example 27

Using the columns of Example 26 filled with the uncoated polyfluorinated resin particles, the columns were washed with 60 column volumes of 5.0 normal sodium hydroxide solution, followed by 60 column volumes of deionized water. The solutes were then reinjected and the same gradient as resulted in Example 26 was observed. In particular, the caustic-washed resin showed the same retention as the resin which had not undergone such washing, thus illustrating the robustness of the particles.

Example 28

This example illustrates the modification of synthesis variables to produce polyfluorostyrene particles of widely different particle size.

TABLE 5

VARIATION OF PROCESS VARIABLES TO MAKE DIVERSE PARTICLE SIZES

| Particle Size, micrometers | 16 | 120 |
|---|---|---|
| Reactants |  |  |
| Deionized water, mL | 660 | 490 |
| Poly(vinyl alcohol), g | 16 | 3.9 |
| Pentafluorostyrene, g | 10 | 39.8 |
| Ethyleneglycol dimethacrylate, g | 14 | 55.7 |
| Dibutyl phthalate, mL | 32 | 127 |
| Azo-bis-isobutynonitrile, g | 0.12 | 0.48 |
| Benzyl peroxide, g | 0.12 | 0.49 |
| Sodium lauryl sulfate, g | 0.06 | None |
| Agitator Speed RPM | 900 | 395 |

Upon review of the performance characteristics of the adsorbents of the invention and comparison of those characteristics with the properties of other widely used adsorbent materials, it is clear from the data in Table 5 above that the polyfluorinated adsorbents of the invention are uniformly high in all the physical and chemical properties which are vital to their function.

TABLE 6

COMPARISON OF THE INVENTION WITH OTHER COMMERCIAL AVAILABLE CHROMATOGRAPHY SUPPORTS

| Matrix | Chemical Stability (ph) | Mechanical Stability | Permeability to Macro-molecules | Non-specific Adsorption | Ease of Derivatization | Resistance to 5N NaOH |
|---|---|---|---|---|---|---|
| Agarose | 4–9 | low | excellent | low | good | poor |
| Crosslinked agarose | 2–14 | low | excellent | low | good | poor |
| Crosslinked dextron | 72 | low | poor | low | good | poor |
| Crosslinked polyacrylamide | 2–10 | medium | poor | low | good | poor |
| Polyacrylamide/dextran | 3–11 | low | excellent | medium | good | poor |
| Polyacrylamide/agarose | 3–10 | medium | good | medium | good | poor |
| Crosslinked hydroxyethyl methacrylate | 1–14 | high | good | high | good | good |
| Silica | 2–9 | high | good | high | poor | very poor |
| Polystyrene/divinylbenzene | 1–14 | high | good | high | good | good |
| Polyfluorinated particle of the invention with hydrophilic surface coating | 1–14 | high | excellent | low | excellent | excellent |

From the data in Table 6, it can readily be seen that the adsorbents of the invention are chemically stable over a very broad pH range and have a high mechanical stability. The invention adsorbents also have excellent permeability to macromolecules and, quite desirably, low non-specific adsorption properties. In addition, the claimed adsorbents have excellent ease of derivatization and excellent resistance to the corrosive effects of SN NaOH solutions. None of the other well-known adsorbents have such uniformly outstanding performance in all of the listed functionally important properties.

We claim:

1. A process for the preparation of porous spherical particles of fluorinated polymer adsorbent comprising the steps:

(1) forming a water-insoluble solution of organic compounds comprising (a) a monomer selected from $C_{2-4}$ alkylene glycol ester of a $C_{3-6}$ acrylic acid, (b) a polyfluorinated monomer having ethylenic polymerization functionality, (c) a free radical initiator and (d) a water-insoluble, organic solvent-soluble porogenic material, the weight ratio of monomers (a) and (b) to porogenic material being 0.5–2;

(2) with high shear agitation, forming a dilute solution of poly(vinyl alcohol) in water from which any oxygen has been purged with inert gas;

(3) with continuing high shear agitation and inert gas purging, rapidly dispersing the water-insoluble solution of organic compounds from step (1) into the dilute aqueous poly(vinyl alcohol) solution from step (2) and adjusting the temperature of the dispersion to 30–90 C. to initiate copolymerization of the monomers, the level of high shear mixing energy being sufficient to disperse the water-insoluble solution of organic compounds in the poly(vinyl alcohol) solution in the form of liquid droplets having an average diameter of no more than 50 micrometers, at least 90% of the droplets being within the range of 20–80 micrometers;

(4) continuing the high shear agitation and oxygen purging of the dispersion from step (3) for a time sufficient to effect complete copolymerization of the monomers and particulation of the droplets in the form of finely divided particles by precipitation of the copolymer therein;

(5) separating the finely divided copolymer particles from the polymerization reaction medium;

(6) extracting the porogenic material from the separated copolymer particles of step (5) by washing the particles with inert organic solvent, thereby forming pores within the copolymer; and (7) drying the porous copolymer particles.

2. The process of claim 1 in which the polyfluorinated monomer is perfluorinated.

3. The method of claim 1 which is carried out at a temperature of 70–90 C.

4. The method of claim 1 in which the polymerization catalyst is selected from azo-bis-isobutyronitrile, benzoyl peroxide and mixtures thereof.

5. The method of claim 1 in which the porogenic material is selected from liquid dibutyl phthlate, a liquid solution of polystyrene in isopropyl benzene, toluene, 2-methyl-4-pentanone, 2-methyl-4-pentanol, chlorobenzene and mixtures thereof.

6. The method of claim 1 in which the polymerization functionality of the fluorinated monomer is selected from acrylic, methacrylic, and styrene.

7. The method of claim 1 in which the comonomers are ethylene glycol dimethacrylate and pentafluorostyrene.

8. The method of claim 1 in which the comonomers are ethylene glycol dimethacrylate and a fluorinated methacrylate.

9. The method of claim 1 in which the comonomers are ethylene glycol dimethacrylate and 2-(N-ethylperfluorooctane sulphonamido) ethyl methacrylate.

10. Finely divided, porous, fluorinated adsorbent particles made by the process of claim 1.

11. The fluorinated adsorbent particles of claim 10 which have been coated with a hydrophilic polymer.

12. The fluorinated adsorbent particles of claim 11 in which the hydrophilic polymer is poly(vinyl alcohol).

13. A method for the separation of chromatographically separable components of a liquid solution comprising passing the liquid solution through a bed of the adsorbent particles of claim 1, by which one component is separated by adsorption onto the surface of the adsorbent particles and the other passes through the column with adsorption on the adsorbent particles.

14. The method of claim 13 for use in conducting reverse phase separations.

15. The method of claim 13 for use in conducting affinity separations.

16. The method of claim 13 for use in conducting expanded bed separations.

* * * * *